United States Patent
Rivera Vega

(10) Patent No.: US 6,905,712 B2
(45) Date of Patent: Jun. 14, 2005

(54) VACCINE ADJUVANTS COMPRISING GINSENG PLANT EXTRACT AND ADDED ALUMINUM SALT

(75) Inventor: Esteban Rivera Vega, Uppsala (SE)

(73) Assignee: Statens Veterinarmedicinska Anstalt, Uppsala (SE)

( * ) Notice: Subject to any disclaimer, the term of this patent is extended or adjusted under 35 U.S.C. 154(b) by 0 days.

(21) Appl. No.: 10/149,119

(22) PCT Filed: Dec. 8, 2000

(86) PCT No.: PCT/SE00/02478

§ 371 (c)(1),
(2), (4) Date: Oct. 18, 2002

(87) PCT Pub. No.: WO01/41802

PCT Pub. Date: Jun. 14, 2001

(65) Prior Publication Data

US 2003/0095975 A1 May 22, 2003

Related U.S. Application Data

(60) Provisional application No. 60/169,613, filed on Dec. 8, 1999.

(30) Foreign Application Priority Data

Dec. 8, 1999 (SE) ............................................. 9904480

(51) Int. Cl.$^7$ ............................................. A61K 35/78
(52) U.S. Cl. ................... 424/728; 424/725; 424/278.1; 424/690
(58) Field of Search .............................. 424/195.1, 725, 424/728, 278.1, 690

(56) References Cited

U.S. PATENT DOCUMENTS

5,817,314 A 10/1998 So et al.
6,083,512 A * 7/2000 Roberts ................... 424/247.1

FOREIGN PATENT DOCUMENTS

WO WO 96/33739 10/1996
WO WO 98/15287 4/1998

OTHER PUBLICATIONS

J. Y. Ro et al., "A single component of ginsenosides extracted from Korean Red Ginseng Radix has an adjuvant activity", West–Pac Allergy Symp. Korean–Jpn. Jt. Allergy Symp., $5^{th}$, $7^{th}$, 171–175. 1997. American Chemical Society abstract.

* cited by examiner

Primary Examiner—Patricia Leith
(74) Attorney, Agent, or Firm—Young & Thompson

(57) ABSTRACT

A composition, which includes ingredients capable of enhancing the immunogenic effect of a vaccine, includes an aluminium salt and at least one ginsenoside, such as a tri-terpenoid glycoside, preferably a tri-terpenoid glycoside of the structure of Rb1. In one particular embodiment, the aluminium salt is Al(OH)3. A kit for use as adjuvant or co-adjuvant of an immunogenic composition includes the composition. The use of such a tri-terpenoid glycoside in the manufacture of a pharmaceutical preparation enhanced the immunogenic effect of a vaccine. A pharmaceutical preparation includes the composition and an aluminium salt, such as Al(OH)3 and a pharmaceutically acceptable carrier.

17 Claims, 2 Drawing Sheets

US 6,905,712 B2

VACCINE ADJUVANTS COMPRISING GINSENG PLANT EXTRACT AND ADDED ALUMINUM SALT

This application is a 371 of PCT/SE00/02478 Dec. 8, 2000 which claim benefit of provisional application 60/169,613 Dec. 5, 1999.

TECHNICAL FIELD

The present invention relates to a new group of adjuvants capable of enhancing the immunogenic effect of antigens used in immunization of mammals. The invention also relates to a method of producing am immunogenic composition comprising the adjuvant according to the invention.

BACKGROUND

Immunization to protect against communicable disease is one of the most successful and cost-effective practices of modern medicine. Smallpox has been completely eliminated by vaccination, and the incidence of many other dreaded diseases such as polio and diphtheria has been drastically reduced through immunization programs. However, vaccines, especially those based on the use of inactivated viruses, vary in effectiveness.

Thus, in order to enhance the immunogenic effects of vaccine compositions, adjuvants are frequently used. Such adjuvants are often aluminum compounds, in the form of hydroxides or phosphates. Through coupling with vaccine antigens, the so-called adsorbate, these aluminium compounds result in vaccines, the immunopotentiation action of which is explained by the resulting vaccine depots, from which the release of antigen for adsorption is retarded. However, the aggregation and settling tendencies of solid aluminium compounds, as well as the behaviour of their residue, is a disadvantage of the use of these compounds. In addition, further problems arise with vaccines adjuvanted with Al-salts due to a number of other reported limitations, e.g.

a) the antibody response is often of short duration,
b) they induce poor cell mediated immunity (CMI) and
c) they can support the production of IgE antibodies which may lead to hypersensitive reactions.

As an interesting alternative to the Al-salts, the saponins extracted from the bark of the tree Quillaja saponaria have been suggested (see, for example, WO98/155287, WO96/33739, U.S. Pat. No. 5,817,314, U.S. Pat. No. 5,977,081). In contrast to the Al-salts, these saponins are able to induce both antibody response and CMI. Therefore, they have been frequently used as adjuvants in veterinary vaccines. Unfortunately, most Quillaja-saponins (Qsaponins) have a strong haemolytical activity and cause undesirable local reactions (Tizard, I. Vaccination and Vaccines. In *An Introduction to Veterinary Immunology* 5th ed. Editor I. Tizard; Philadelphia, London, Tokyo, 1996, 265–284; and Horzinek, M. C., Schijns, V.E.C.J., Denis, M., Desmettre, P. and Babiuk, L. A. General Description of Vaccines. In *Veterinary Vaccinology*, ed. P. P. Pastoret, Blancou, J., Vannier, P. and Verschueren, C., Elsevier Science, Amsterdam, New York, Tokyo. 1997, 131–152), which limits their use in vaccines for large animals. Moreover, the ginsenoside-saponins from the Korean Red Ginseng Radix has been proposed to show adjuvant activity in its pure form. However, to purify a single ginsenoside is a costly process.

Thus, this far, saponins have not seemed to constitute ideal adjuvants either. Although the literature contains many reports describing new adjuvants, most vaccines recommended for human or veterinary use still contain aluminium salts (Al-salts) as the adjuvant, despite the above discussed disadvantages thereof. Conclusively, at present, there is still a need within this field for novel adjuvants, or at least for methods of reducing the amount used of the hitherto used Al-salts.

SUMMARY OF THE PRESENT INVENTION

The present invention solves the problems defined above by providing a novel composition comprising efficient and safe ingredients capable of exerting specific and highly efficient adjuvant properties to a vaccine administered before, after or simultaneous with said ingredients. The composition of the invention is capable of enhancing the immunogenic effect of a vaccine, comprises an extract of a ginseng plant and an aluminium salt, and is obtainable by a method comprising the steps of:

(a) providing an extract of a ginseng plant, which extract comprises at least one ginsenoside;
(b) adding an aluminium salt to the extract.

Preferably, the composition according to the invention is an extract from a Ginseng root, and preferably Panax ginseng root.

Advantageously, a ginseng extract, which comprises triterpenoid glycosides, including the $Rb_1$ structure disclosed below, is combined in the composition of the invention with an aluminium salt, such as $Al(OH)_3$. Said combination has according to the present invention shown to be highly efficient due to a synergistic effect of said two ingredients, which effect will be described in detail below. The Rb1 structure is preferably included at a vaccine dose of approximately 166 µg. More preferably, the extract comprises one or more, most preferably all, of the ginsenosides Rg1, Re, Rb1, Rc, Rb2 and Rd, as well as any of the other 28 known ginsenoside compounds.

In addition, the present invention relates to a kit comprising the composition for use as adjuvant or co-adjuvant of an immunogenic composition as well as to the use of such a composition in the manufacture of a pharmaceutical preparation for enhancing the immunogenic effect of a vaccine. Further, the invention also relates to a pharmaceutical preparation manufactured by the present use, which pharmaceutical preparation further comprises a pharmaceutically acceptable carrier.

DEFINITIONS

Figure 1:
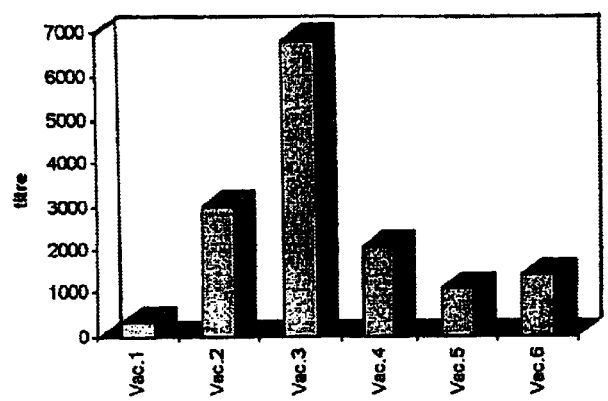
FIG. 1 shows the antibody response induced by different Porcine Parvovirus (PPV) vaccines as measured by HI-tests (Example 1 of the present invention).

In the present application, the term "adjuvant" means any substance or compound capable of promoting an increased immune response in a mammalian species, e.g. by modifying the activities of cells that are concerned with generating and maintaining the immune response or by modifying the presentation of antigen to the immune system.

As used herein, the term "vaccine" means any compound or preparation of antigens designed to stimulate a normal primary immune response, resulting in proliferation of the memory cells and the ability to exhibit a secondary memory or anamnestic response upon subsequent exposure to the same antigens.

With "comprising the structure of $Rb_1$" is meant that said structure, which is illustrated below in the section "Detailed description of the invention", constitutes an essential and functional part. Thus, further molecules may have been added or minor changes may have been made, as long as the essential character thereof which provides the herein disclosed function of adjuvant remain.

DETAILED DESCRIPTION OF THE INVENTION

Thus, in a first aspect, the present invention relates to a composition, which comprises ingredients capable of enhancing the immunogenic effect of a vaccine, and which composition is obtainable by a method comprising the steps of: (a) providing an extract of a ginseng plant, and (b) adding an aluminium salt to the extract. More specifically, the composition according to the invention comprises an extract from ginseng root, preferably Panax ginseng root, e.g. in amounts of about 1–20 mg, such as about 1–15 mg, e.g. about 1–10 mg and more specifically about 2 mg, ginseng for each vaccine dose. Ginseng-dry extracts have been analysed and established to contain a number of active substances, e.g. ginsenosides which are a kind of saponins, chemically tri-terpenoid glycosides of the dammaran series, see e.g. Liu, C. X., and Xiao, P.G. Review Article, Recent advances on ginseng research in China, *J. of Ethnopharmacology*, 1992,36,27–38. Thus, in the most preferred embodiment of the invention, the extract will comprise at least one tri-terpenoid glycoside, preferably with the structure of $Rb_1$ as defined by formula (I) below:

(I)

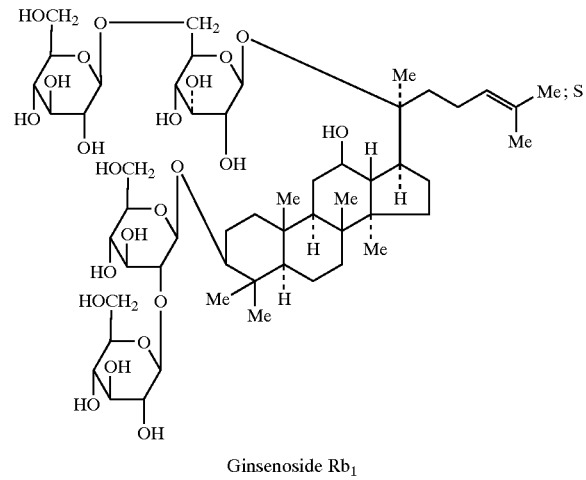

Ginsenoside $Rb_1$

Accordingly, the ginsenosides extracted from the Panax ginseng C. A. Meyer-root are tri-terpenoid glycosides of the dammaran series that according to the present invention have proved to exhibit a strong adjuvant effect, while being safe and without the above discussed disadvantages. Thus, apart from inducing an antibody response, compared to previously tested saponins, the present ginsenosides have other advantageous properties, which make them promising adjuvants, e.g.:

1) they appear to be much safer than the previously suggested Q-saponins, as shown in the present ginseng-safety studies, which showed no local or general side effects. Other studies which support the present observations report that the oral administration in rabbits of 2000 mg ginseng/kg for seven days had no effect on body weight, blood, chemical or clinical parameters. The ginseng-LD/50 for mice is 950 mg/kg (Tang, W. and Eisenbrand, G. Panax ginseng C. A. Mey. In *Chinese Drugs of Plant Origin*, ed. W. Tang and G. Eisenbrand, Springer-Verlag, Berlin, New York, London, Tokyo. 1992, 711–737).

2) Contrary to Q-saponins, ginseng almost completely lacks haemolytic activity as demonstrated in the present table 2, and in previous studies (Namba, T., Yoshizaki, M., Tomimori, T., Kobashi, K., Mitsui, K. and Hase, J. Fundamental studies on the evaluation of the crude drugs. I. Hemolytic and its protective activity of ginseng saponins. *Planta Med.*, 1974, 25, 28). Since the side effects reported for the use of the Q-saponins are linked to their haemolytic activity (Kensil et al., 1991, supra; and R önnberg et al., 1995, supra), it is probable that the differences between both adjuvants regarding haemolytic activity could explain why ginseng is so safe.

3) The present ginsenosides trigger the immune system (see Example 3, FIG. 2) in such a manner that posterior antigen injection leads to an increased specific-antibody response, indicating that the treatment of low responders with ginseng may provide them with a better immunization.

4) The present ginsenosides are safe for the stomach and resist the gastric secretions. Therefore, as discussed below, they are contemplated as suitable adjuvants for oral vaccines.

5) The present invention concerns an extract comprising ginsenosides and an aluminium salt, as well as other ingredients, which is shown to have a stronger adjuvant activity, than the pure ginsenosides when tested alone (table 6).

Thus, the present inventors have for the first time disclosed advantageous use of an extract of the ginsenosides as a vaccine adjuvant, even though ginseng has previously been shown to exhibit advantageous properties in relation to health aspects. For example, according to the old Chinese Pharmacopoeia, written more than 2000 years ago, the extract obtained from the Panax ginseng C. A. Meyer-root and named ginseng has been used in the Chinese medicine for different purposes e.g. as a stimulant of the central nervous system, increasing mental concentration or as an anti-stress, and as a general tonic improving the natural resistance against infections. More recently, studies demonstrate that the ginseng support-cell proliferation. Ginseng also promotes the phagocytic activity of human alveolar macrophages as well as the oxidative and phagocytic activities of the bovine polymorphonuclear leukocytes. However, as mentioned above, it has never been shown before to exhibit adjuvant or coadjuvant properties when used with vaccines against pathogenic microorganism.

Thus, in the most advantageous embodiment, the composition according to the present invention will further comprise an aluminium salt, such as $Al(OH)_3$. According to the present invention, it has quite unexpected been shown that the use of ginseng and aluminium trihydroxide provides a clearly synergistic effect, as compared to the added effects of $Al(OH)_3$ and ginseng used separately. While the conventionally used hydroxides have been used in the experiments in the present application, any other salt of aluminium, such as aluminium phosphate or aluminium sulphate, or alums, such as ammonium alum or potassium alum, may equally well be used in the present context, as long as it's chemical properties are sufficiently similar to the $Al(OH)_3$ used herein.

More specifically, using a haemagglutination inhibition (HI) test in the antibody titration, it was found that the mean HI-titre for the animals injected with PPV antigen only was 320±0. By comparison, the mean titre value was 2026±1206 for the sera from the animals injected with the same vaccine but adjuvanted with 4 mg of ginsenoside, while the antibody titre induced by a vaccine containing 50% $Al(OH)_3$-gel was 2986±1596. In addition, the ginsenoside and $Al(OH)_3$ acted synergistically and further improved the antibody response to the PPV antigen to 6826±2413. Moreover, vaccines containing ginsenoside as adjuvant induced the production of virus-neutralising antibodies; this was demonstrated by neutralisation assays using PK-15 cells and live PPV virus. Furthermore, it was demonstrated that the immunomodulatory effect of the ginsenoside is dose-dependent and that the ginsenosides are safe adjuvants when injected subcutaneously in guinea pigs, mice and minks or intramuscularly in pigs. The ginsenoside have a very low haemolytic activity on the red blood cells of swine, cattle, chicken or guinea pigs.

Accordingly, in a preferred embodiment and best mode of the present invention, the present composition will comprise $Rb_1$ within a range of 5–500 μg, such as about 40–250 μg, e.g. about 60–175 μg and preferably about 80 μg to about 100 μg/vaccine dosage. In the present context, it is to be understood that when an adjuvant according to the present invention is prepared, the tri-terpenoid glycoside is not restricted to tri-terpenoid glycosides extracted from ginseng, if they may be prepared in other ways. Thus, the present $Rb_1$ may originate e.g. from chemical synthesis, even though it was first discovered by using an extract of ginseng. Examples of useful amounts of aluminium salt used in combination with said $Rb_1$ amount are presented in the experimental part of the present specification, but it appears that the amount of aluminium salt is not critical. Thus, the quantity of aluminium in the present composition is not limited to the ones shown in the examples. Rather, since $Al(OH)_3$ has been used for some time, ideal concentrations for PPV-vaccines has been established and put in use (Joo, H. S., Molitor, T. W. and Leman, A. D. Antibody responses of guinea-pigs, rabbits and pigs to inactivated porcine parvovirus vaccines, *Veterinary microbiol.*, 1989, 9, 27–33; Rivera, E., Sjösten, C. G., Bergman, R. and Karlsson, K. A. Porcine parvovirus: propagation in microcarrier cell culture and immunogenic evaluation in pregnant gilts, *Res. Vet. Sci.*, 1986, 41, 391–396; and Lei, J. C., Overby, E., Holm-Jensen, M. and Sörensen F. O. Preparation of a porcine parvovirus vaccine. *Proc. Int. pig vet soc., Copenahagen*, 1980, 64), which concentrations are also useful in the present context.

However, as a general principle, the novel advantageous synergistic effect of ginseng, specifically of tri-terpenoid glycosides, such as $Rb_1$, combined with an aluminium salt provides an improved adjuvant effect without need of increasing the amount of $Al(OH)_3$, thus avoiding the disadvantages of large quantities of aluminium discussed above. In other words, by using ginseng as co-adjuvant it appears to be possible to minimise the total amount of Al-salts in vaccines, thereby minimising the risk e.g. for allergies. Further, as ginseng induces interferon production and stimulates the activity of cytotoxic T-lymphocytes, the use of ginseng as a co-adjuvant in the Al-salts adjuvanted vaccines is contemplated to lead to better immunizations in many aspects.

Furthermore, in one specific embodiment, the invention relates to a kit comprising the ginseng and aluminium salt ingredients formulated into one single adjuvant composition, optionally together with a pharmaceutically acceptable carrier, such as sterile water or saline. The present kit may further be prepared with sufficient amounts for one or more booster administrations, thus adapted for single administrations or a series of administrations. As shown below, it does not appear to be critical whether the present adjuvant is injected before, after or simultaneously with the vaccine, even though conventionally the adjuvant and the antigen are simultaneously administered. Thus, according to the present invention, it has been shown that ginseng improves the antibody response to the PPV antigen regardless of the administration procedure used (see Example nos.1, 2 and 3).

As mentioned above, the ingredients of the present kit may be administered parenterally, e.g. subcutaneously or intramuscularly, even though other methods, such as injections also are contemplated, as well as oral administration. The skilled in this field will decide for each instance the suitable way of delivery, and for a brief review of methods of drug delivery, see e.g. Langer, *Science* 249:1527–1533 (1990).

Advantageously, the present kit will also include written instructions regarding the use thereof, optionally also means for administration, etc., in a suitable container.

In a second aspect, the present invention relates to an extract comprising tri-terpenoid glycosides, preferably comprising the structure of $Rb_1$, for use as an adjuvant for use to enhance the immunogenic properties of a vaccine as well as to the use of a tri-terpenoid glycoside, preferably comprising the structure of $Rb_1$, in the manufacture of a pharmaceutical composition effective as adjuvant, or in the manufacture of a complete vaccine comprising such adjuvant. Such pharmaceutical compositions will be disclosed in further detail below. In addition, the invention also includes a tri-terpenoid glycoside, preferably comprising the structure of $Rb_1$, together with an aluminium salt for use as a medicament aimed at treating conditions characterized by a weakened immune system.

Thus, the invention also relates to a method of immunization, wherein an extract from ginseng root, preferably Panax ginseng root, is administered before, simultaneously with or after the administration of an immunogenic substance to enhance the effect thereof. Preferably, said extract comprises a tri-terpenoid glycoside of the dammoran series, preferably comprising the structure of $Rb_1$ of formula (I) as defined above. In the preferred embodiment and best mode of the present method, said extract is administered as a co-adjuvant with an aluminium salt, such as $Al(OH)_3$, wherein the ginseng is administered so as to provide an amount of about 5–500 μg, preferably from about 80 μg to 100 μg, of $Rb_1$.

In a further aspect, the invention relates to a pharmaceutical preparation for use in a method as defined above, wherein ginseng, such as the tri-terpenoid glycoside, has been combined with a pharmaceutically acceptable carrier, and/or supplemented with further excipients or additives. In the preferred embodiment and best mode, the present preparation further comprises an aluminium salt, such as $Al(OH)_3$, while the tri-terpenoid glycoside is $Rb_1$ of the above defined formula (I) in amounts as defined above. (General methods for the manufacture of pharmaceutical preparations are e.g.

found in Remington's Pharmaceutical Sciences, 16th ed., Osol, A. (ed), 1980.)

In a specific embodiment of the last mentioned aspect, the present kit includes the vaccine in addition to the above discussed ingredients formulated into one single composition. In that case, in addition to antigen and the present adjuvant(s), the formulation may comprise a hydrating agent (e.g., liposomes), a penetration enhancer, or both. For example, the formulation may comprise AQUAPHOR (an emulsion of petrolatum, mineral oil, mineral wax, wool wax, panthenol, bisabol, and glycerin), emulsions (e.g., aqueous creams), oil-in-water emulsions (e.g., oily creams), anhydrous lipids and oil-in-water emulsions, anhydrous lipids and water-in-oil emulsions, fats, waxes, oil, silicones, and humectants (e.g., glycerol). For a more detailed discussion of methods of vaccine manufacture, reference is made to suitable literature.

The vaccine of the invention may be used for treating any state or disease, even though treatment of gastric or intestine diseases or states, such as diarrhea, may be mentioned.

In the preparation of vaccines, it is noted that although licensed vaccines are supposed to be produced following well-established procedures, the licensed vaccines used in the experimental part below differed in their immunogenic capacity. Thus, specific attention must be used by the skilled in this field when the production of homogeneous vaccine batches is desired, due to the lack of methods at present for in-process controlling and measuring the production of the 64–66 kD-protective antigen by the *E. rhusiopathiae* bacteria. Bacterial count is at present not accurate enough since the expression of the *E. rhusiopathiae*-protective antigen may vary from culture to culture. Another factor affecting the final product of the vaccine is the binding capacity of the adjuvant, which in the case of aluminium hydroxide may also vary. Thus there will remain a need for the skilled in this field to perform some further experimentation, such as measurements of the correct proportion of the protective antigen of *E. rhusiopathiae* in the present vaccines or alternatively in the adjuvants or in both.

DETAILED DESCRIPTION OF THE DRAWINGS

FIG. 1 shows the antibody response induced by different PPV vaccines as measured by HI-tests (Example 1, below). Vac.no.1 contained PPV virus only, vac.no.2 contained virus and aluminium hydroxide, vac.no.3 was a double adjuvanted vaccine containing aluminium hydroxide and ginseng, vac.no.4 and vac.no.5 contained 4 or 2 mg of Chinese ginseng respectively and vac.no.6 contained 2 mg of Italian ginseng. Each bar represent the group titre mean value.

Figure 2:
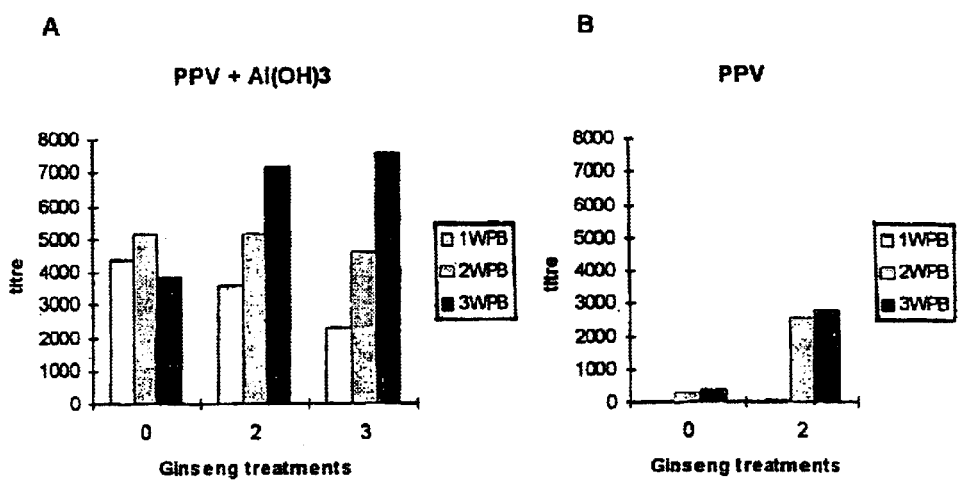
FIG. 2 shows the effect of the pre-treatment with ginseng on the antibody response of guinea pigs to PPV virus (Example 3 of the present invention), A being animals immunized with $Al(OH)_3$ adjuvanted PPV-vaccines while B is with PPV only.

FIG. 2 shows the effect of the pre-treatrnent with ginseng on the antibody response of guinea pigs to PPV virus (Example 3, below). Groups of animals were immunized with Al(OH)$_3$ adjuvanted vaccines (A) or with PPV only (B). Each bar represents the group titre mean value.

Figure 3:
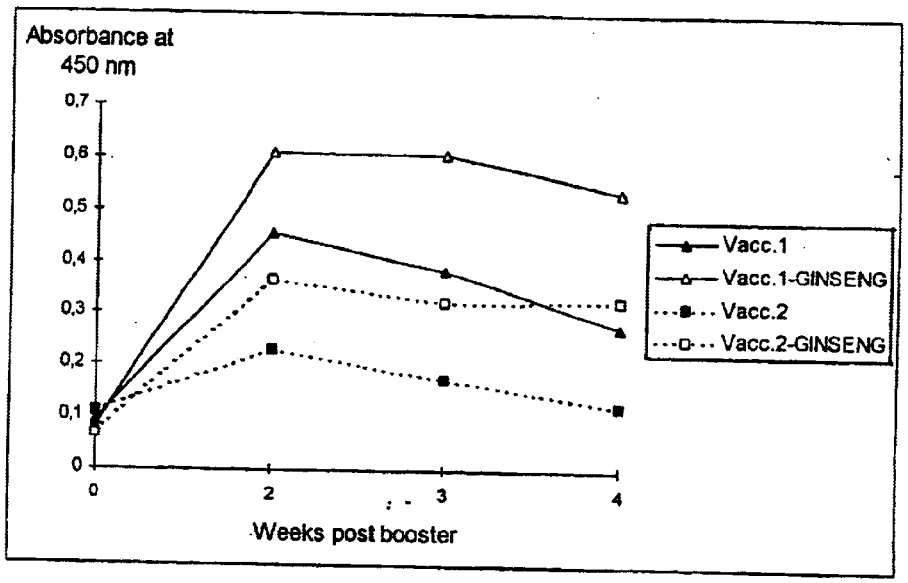
FIG. 3 shows a determination of the antibody response to *Erysipelothrix rhusiopathiae* as assayed by ELISA.

FIG. 3 shows a determination of the antibody response to *Erysipelothrix rhusiopathiae* as assayed by ELISA. The results are presented as the group mean absorbance measured at 450 nm.

Figure 4:
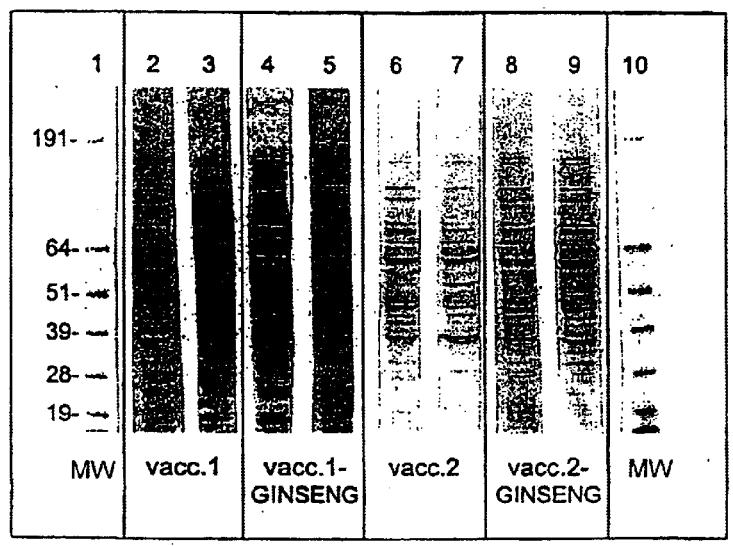
FIG. 4 shows a determination of the antibody response to *Erysipelothrix Rhusiopathiae* as assayed by immunoblotting.

FIG. 4 shows a determination of the antibody response to *Erysipelothrix Rhusiopathiae* as assayed by immunoblotting. Sera from individual pigs, lane 2–9, were tested 3 weeks post booster. Lane 1 and 10; prestained molecular weight markers.

EXPERIMENTAL

Below, the present invention will be described by way of examples, which are only to be construed as illustrating the invention and not limiting the scope thereof as defined by the appended claims. All references below and elsewhere in the present application are hereby included herein by reference.

The present experimental section has been divided into two parts, part I and part II. In part I, it is demonstrated that ginseng is a safe adjuvant and that ginseng and aluminium hydroxide act synergistically resulting in a potent adjuvant combination which induces the production of higher antibody titres than do either adjuvant when used alone. In part II, it is demonstrated that the immunogenic potency of aluminium-hydroxide adjuvanted vaccines against PPV and *Erysipelothrix rhusiopathiae* infections can be improved by using ginseng as a vaccine co-adjuvant. In order to facilitate the reading, the experimental section has been disposed as follows:

Disposition

Part I

1. Material and methods
1.1 Ginseng extracts
1.2 Cell cultures and virus propagation
1.3 Virus antigen preparation
1.4 Adjuvants
1.5 Vaccines
2. Examples
2.1 Example 1: Effect of ginseng
2.2 Example 2: Injection procedure
2.3 Example 3: Activation of immune system
2.4 Example 4: Serological Tests
2.5 Example 5: Safety Tests
2.6 Example 6: Assay of Haemolysis
2.7 Example 7: Absorption Assays
3. Results
3.1 Results of Example 1: Ginseng and Al(OH)$_3$ Act synergistically . . .
3.2 Results of Example 2: Ginseng Exerts Its Adjuvanting Effect Even . . .
3.3 Results of Example 3: Ginseng Triggers the Immune System
3.4 Results of Example 4: Serological Tests
3.5 Results of Example 5: Safety Tests
3.6 Results of Example 6: Assay of Haemolysis
3.7 Results of Example 7: Absorption Assays Part II 4. Materials and methods
4.1 Ginseng
4.2 Antigens
4.3 Vaccines
4.4 Vaccination of pigs
5. Examples
5.1 Example 1: Erysipelas mouse potency test (immune response)
5.2 Example 2: Haemagglutination inhibition assay (antibody response)
5.3 Example 3: ELISA (immune response)
5.4 Example 4: Immunoblotting
5.5 Example 5: Safety
6. Results
6.1 Results of Example 1: Mouse potency test (immune response)

6.2 Results of Example 2: Haemagglutination inhibition assay (antibody response)
6.3 Results of Example 3: ELISA
6.4 Results of Example 4: Immunoblotting
6.5 Results of Example 5: Safety Part III 7. Haemagglutination inhibition test
8. Ginseng extract HPLC analysis
9. Discussion: Part I and Part II Part I Below, it will be shown that the ginsenosides (GS-De) contained in the extract prepared from the Panax ginseng C. A. Meyer-root have adjuvant properties as demonstrated by
a) injecting guinea pigs with a mixture of the GS-De and the inactivated porcine parvovirus (PPV) antigen as a conventional vaccine,
b) injecting the PPV antigen and the GS-De simultaneously but separately at different places on the animal or
c) injecting only the GS-De one or two weeks prior to immunization with the PPV antigen.

1. MATERIAL AND METHODS

Vaccines were prepared containing different amounts of ginseng (=ginsenosides) but constant amounts of PPV-antigen and tested them using guinea pigs as experimental animals. Guinea pigs (GPs) were chosen for testing the vaccines because GPs are recommended as suitable animals for testing the immunogenicity of vaccines against porcine parvovirus infection in the pig (Joo et al., 1989, supra). In addition, since most available vaccines for veterinary use (including PPV vaccines) contain aluminium-hydroxide gel as adjuvant (Morein, B., Lövgren-Bengtsson, K. and Cox, J. General principles of vaccinology, Modern adjuvants. Functional aspects. In *Concepts in Vaccine Development*, Ed. S. H. E. Kaufmann. Berlin; New York; De Gruyter, 1996, 243–263; and Tizard et al., 1996, supra; and Horzinek et al., 1997, supra), such an adjuvanted PPV-vaccine was used as a reference vaccine in the present experiments.

1.1 Ginseng Extracts

Two ginseng dry extracts were evaluated as adjuvant for PPV vaccines; both extracts were prepared from the Panax ginseng C. A. Meyer-root and contained similar amounts of the protopanaxatriol ginsenosides Re and Rg1. The ginseng extracted in China was kindly provided by the Pharmaceutical Co. Ltd. (Chiatai Qingchubao, China); in this study it is referred to as CH-GS. The ginseng extracted in Italy was provided free of charge by the Indena SPA company (Italy) and is referred to as IT-GS.

1.2 Cell Cultures and Virus Propagation

The PK-15 cell line was used to propagate the PPV virus, to control virus inactivation and in the serum neutralisation assays. The cells and the virus were cultured as described previously (Rivera et al., 1986, supra).

1.3 Virus Antigen Preparation

A harvest of PPV virus was clarified by filtration through a 0.25 μm filter. Thereafter, the filtered virus material, containing 2048 haemagglutinating units (HAU) per 0.05 ml, was inactivated with formalin at a final concentration of 0.2% (v/v). Virus inactivation was carried out at 37° C. for three weeks. The absence of residual live virus was demonstrated by serially passing (4 passages) the formalinised virus material in PK-15 cells. After the fourth passage, the cells were fixed by immersing the specimens in a 20% acetone bath (Rivera et al., 1986, supra) and stained using mouse anti-PPV-monoclonal antibodies (Rivera, E., Grönvik, K. O. and Karlsson, K. A. A new method for rapidly removing contaminating micro-organisms from porcine parvovirus or pseudorabies virus master-seed suspensions. *Vaccine*, 1993,11, 363–365) and HRPO-conjugated goat anti-mouse antibodies (Bio Rad Laboratories, Richmond, Calif., USA). The inactivated virus was diluted with physiological sodium chloride solution (NaCl-sol.) until it contained 256 HAU per 0.05 ml. After adjusting the pH to 7.2, the diluted virus (dil-virus) was used in the vaccine preparations.

1.4 Adjuvants

The following adjuvants (alone or in combination) were assayed:
a) 3%-Al(OH)$_3$ gel (Alhydrogel, Superfors A/S; Denmark),
b) Chinese ginseng, i.e. CH-GS,
c) Italian ginseng, i.e. IT-GS,
d) a mixture of Al(OH)$_3$ and CH-GS,
e) NaCl-solution instead of adjuvant.

1.5 Vaccines

Six vaccines were prepared, all preparations contained the same amounts of PPV antigen and had the same final volume (2 ml) per vaccine dose.

Equal volumes of PPV-dil-virus and one of the adjuvant listed above were mixed as follows:
Vaccine (vac.) No. 1 contained dil-virus and NaCl-solution instead of adjuvant (aqueous vaccine).
Vac. No. 2 contained 3%-Al(OH)$_3$ as adjuvant.
Vac. No. 3 contained double adjuvant and was a mixture of dil-virus containing 2 mg CH-GS/ml and 3%-Al(OH)$_3$.
Vaccines No. 4 and No. 5 were mixtures of dil-virus and NaCl-solutions containing (per ml) 4 or 2 mg. CH-GS, respectively.
Vac. No. 6 included IT-GS as adjuvant at a concentration of 2 mg.per ml NaCl-solution.

2. EXAMPLES

The specific pathogen-free guinea pigs (GPs.) used in the evaluation of the vaccines were obtained from the National Veterinary Institute (S-75007 Uppsala, Sweden). The animals were divided into groups of four or five animals according to the experiment and were kept isolated during the evaluation of the vaccines. Three experiments were carried out.

2.1 Example 1

The Adjuvant Effect of Ginseng

The first experiment was carried out to ascertain whether ginseng has a adjuvant effect or not, to compare its effect with the one obtained using Al(OH)$_3$ and to investigate if ginseng and Al(OH)$_3$ possibly act synergistically. For this experiment, 24 GPs were divided into six groups and they were injected subcutaneously with 2 ml of one of the vaccines described above. The animals received two vaccine doses at 3 week intervals. Blood samples were taken 2 weeks after the second injection.

2.2 Example 2
The Optimal Injection Procedure

This experiment was designed to determine the number of injections needed for an optimal immunization using ginseng adjuvanted vaccines and to ascertain whether or not the antigen and ginseng bind together and build a complex.

For this experiment, 22 GPs were divided into four groups of five GPs each and one group of two GPs (negative control animals). The animals included in group 1 were vaccinated once with a mixture of 1 ml dil-virus and 1 ml NaCl-solution containing 1 mg of CH-GS. The animals included in group 2 were vaccinated twice at three week intervals using the same vaccine as for group 1. The GPs in group 3 were injected once with 1 ml dil-virus and with one ml NaCl-solution containing 1 mg of CH-GS. Both preparations were injected simultaneously but each of them at different sites on the animals. The GP in group 4 were immunized in the same way as group 3, but on two occasions with a three week interval. The animals included in group 5 received two injections of NaCl-solution. Blood samples were taken as follows: 3 weeks after the first vaccination, and both one and three weeks after the booster dose.

2.3 Example 3
Activation of Immune System By Using Ginseng

The aim of this experiment was to investigate if ginseng activates the immune system in an unspecified manner, triggering it for an enhanced antibody response upon antigen injection or immunization using a conventional vaccine. To test the hypothesis, and prior to the immunizations using viral antigen, the animals were either treated with 2 mg of CH-GS or not treated at all. The ginseng was given diluted in NaCl, subcutaneously, on two or three occasions. Then, the animals were immunized twice at a three week interval, using the $Al(OH)_3$-adjuvanted vaccine or dil-virus without adjuvant. In this experiment, 25 GPs were divided into 5 groups. The GPs in group 1 received in total three doses of ginseng and two doses $Al(OH)_3$ adjuvanted vaccine. The two first doses of ginseng were given with a weeks interval, 2 and 1 week before primary vaccination. The third dose of ginseng was given one week before re-vaccination.

The GPs in group 2, received two doses of CH-GS, and two doses of $Al(OH)_3$ adjuvanted vaccine. Ginseng was given two weeks before the first vaccination and one week before re-vaccination.

The animals in group 3 were not treated with ginseng, but they were vaccinated twice with the $Al(OH)_3$-adjuvanted vaccine.

The animals in group 4 were treated with ginseng in the same way as the animals included in group 1 except that they were immunized twice using 1 ml dil-virus without any adjuvant. The animals in group 5 were not treated with ginseng but they were vaccinated twice with the vaccine used for group 4. Blood samples were taken three weeks after primary vaccination and both one and three weeks after the booster dose.

2.4 Example 4
Serological Tests

The antibody response to PPV virus was determined by means of haemagglutination inhibition (HI) and serum neutralisation (SN) tests. The HI test was carried out in V-type microplates using a 0.5% suspension of GP red-blood cells and 16 HAU of PPV virus. The SN-test was carried out in flat bottomed microplates using freshly trypsinised cells and TCID 100/0.1 ml PPV virus. Virus infected cells were detected by means of anti-PPV monoclonal antibodies (Rivera et al., 1993, supra) and peroxidase-conjugated goat anti-mouse antibodies (Bio Rad Laboratories, Richmond, Calif., USA.). The substrate used was 3-Amino-9-ethylcarbazole (AEC).

2.5 Example 5
Safety Tests

The safety of the CH-GS was proven by injecting it subcutaneously into mice, guinea pigs and minks or intramuscularly in pigs. After injections, the mice and guinea pigs were observed daily for a week; the period of observation for minks and pigs was six weeks. Deviations from their normal behaviour or reactions at the injection site were recorded. The 25 NMRI-mice were divided into groups of five animals each and were inoculated either with 100, 50, 20 or 10 micrograms of CH-GS which had been re-suspended in 0.5 ml NaCl-sol. Control mice received 0.5 ml of NaCl-sol. The weight of the mice was controlled at day 0 and at day 4 and 7 post injection. The 8 guinea pigs were divided into groups of two animals each and were injected either with 4, 2 or 1 mg of CH-GS re-suspended in 2 ml NaCl-sol.; the two control animals received NaCl-sol. The 20 minks were divided into groups of five animals each and were injected subcutaneously with 500, 100 or 50 micrograms ginseng in one ml NaCl-sol. The 9 pigs were injected twice with 2 mg CH-GS diluted in 2 ml of NaCl-sol. The injections were given intramuscularly in the neck, at a 3 week interval.

2.6 Example 6
Assay of Haemolysis

The haemolytic activity of the CH-GS was assayed by incubating the ginseng with red blood cells (RBC's) from guinea pig, swine, cattle and chicken. In short, the assay was carried out as follows: RBC's from the species listed above were washed 3 times using NaCl-sol and low speed centrifugation (800 rpm, 10 min). Thereafter, the RBC's pellets were re-suspended at a concentration of 0.5% in 0.01 M PBS, pH 7.2 containing 0.05% v/v of bovine serum albumin. Then, the RBC's preparations were mixed with equal volumes of NaCl-solutions containing CH-GS at concentrations ranging from 100 to 2000 micrograms/ml preparation. The RBC's preparations were also incubated together with an ammonium chloride ($NH_4Cl$) solution to obtain haemolysis-positive controls. The mixtures were incubated at 37° C. for one hour. Thereafter, the samples were centrifuged as described above. Next, the optical density of the supernatants was measured at 414 nm.

2.7 Example 7
Absorption Assays

Preparations of ginseng (CH-GS) at a concentration of 2 mg per ml NaCl were mixed with equal volumes of $Al(OH)_3$-gel or NaCl. The mixtures were continuously stirred at RT° C. for 24 hours. Thereafter, the mixtures were centrifuged at 2000 rpm for 20 min. The supernatants were sent to China for measuring the amounts of free ginseng using high performance liquid chromatography. In another experiment, the vaccine containing double adjuvant $Al(OH)_3$ and CH-GS was also centrifuged as described above and the supernatant was tested for the presence of free PPV antigen by means of a haemagglutination test.

3. RESULTS

3.1 Results of Example 1
Ginseng and $Al(OH)_3$ Act Synergistically Improving the Antibody Response to PPV The results from the HI tests presented in FIG. 1 show that the mean value of the antibody titre to PPV recorded for the sera from the animals immunized with the vaccine containing 4 mg. CH-GS (vac.no.4) was 6.3 fold higher than the mean value recorded for the sera from the GPs injected with the aqueous vaccine without adjuvant (vac.no. 1). FIG. 1 also shows that the ginseng effect is dose-dependent and that at the concentrations compared in this experiment, the CH-GS and IT-GS have a similar effect.

The $Al(OH)_3$ adjuvanted vaccine (vac.no.2). was found to be more potent than the vaccine adjuvanted with 4 mg. CH-GS. However, the use of ginseng and $Al(OH)_3$ in the same vaccine further potentiated the antibody response to the PPV antigen from 2986±1596 to 6826±2413, inducing the highest antibody titres recorded in this experiment (FIG. 1).

3.2 Results of Example 2

Ginseng Exerts Its Adjuvant Effect Even When Injected Separately From the Antigen As seen in Table 1 shown below, two injections are needed for optimal immunization using ginseng adjuvanted vaccines. Three weeks after only one injection, the antibody response induced by all vaccines tested was poor or not detectable at all. However, one week after the booster dose the antibody titres rose rapidly in the serum from the re-vaccinated animals (groups 2 and 4)but remained low in the sera from those not re-vaccinated (groups 1 and 3). As shown below, two weeks after the second injection, the antibody titres continued to increase in the sera from the re-vaccinated animals.

TABLE 1

Experiment no. 2: Determination of the number of injections needed for optimal immunization using ginseng-adjuvanted vaccines. *PPV and ginseng were mixed together and given in one injection or **PPV and ginseng were injected separately at different sites of the animal.

| Group | Number of Vaccinations | HI-titres at Booster | 1. WPB[1] | 2. WPB[1] |
|---|---|---|---|---|
| 1 | 1* | <10 | 10 ± 0 | 10 ± 0 |
| 2 | 2* | <10 | 352 ± 85 | 704 ± 234 |
| 3 | 1** | <10 | 10 ± 0 | 10 ± 0 |
| 4 | 2** | <10 | 353 ± 94 | 960 ± 320 |
| 5 | 0 | <10 | <10 ± 0 | <10 ± 0 |

[1]WPB week post booster

The results from the experiment no.2 also show that ginseng exerts its adjuvant effect regardless of the vaccination procedure. This can be seen by comparing the antibody mean titre value recorded for the groups 2 and 4 (Table 1) which received the same amounts of virus antigen and adjuvant except that the vaccine components were mixed together before injection (for group 2) or were injected separately (group 4). That ginseng exert an adjuvant effect regardless of it administration procedure is further demonstrated by the results from the exp.no.3 (FIG. 2)

3.3 Results of Example 3

Ginseng Triggers the Immune System

In FIG. 2 it is shown that treatment with ginseng prior to vaccination with PPV-antigen lead to increase specific antibody response. The triggering effect of ginseng on the immune system can be more clearly seen by comparing the results recorded for the animals included in the groups 3 and 4 and which were injected with PPV-virus without adjuvant (FIG. 2). At the end of the experiment, the mean antibody titre for the treated animals was 2816 vs 352 for the non-treated ones. Ginseng also improved the antibody response of the animals injected with the $Al(OH)_3$-adjuvanted vaccine. As can be seen in FIG. 2, the antibody titres for the ginseng treated animals (groups 1 and 2) increase continuously while the antibody response for the non-treated animals (group 3) rich the highest titre by week two post booster. Thereafter, the titre begin declining. At the end of the experiment the titres recorded for the treated animals were 7608 and 7168 vs 3840 for the non-treated ones. On the other hand, it seems that two treatments with ginseng are enough for obtaining a good triggering effect of the immune system.

3.4 Results of Example 4

Serological Tests

The quantitative antibody response to PPV-virus assayed by HI-tests is reported in the FIGS. 1 and 2 and in Table 1. The qualitative antibody response assayed by the SN-tests demonstrated that the antibodies produced after vaccinations with ginseng adjuvanted vaccines are virus-neutralising-antibodies as demonstrated by the absence of virus positive cells (data not shown).

3.5 Results of Example 5

Safety Tests

All animals used for testing the safety of ginseng remained clinically healthy during the entire period of the experiments. Neither local reactions nor alterations in the animals behaviour were observed. The mean body-weight recorded for the mice injected with the highest dose of ginseng was 18.78 g and 20.34 g at the beginning and the end of the experiment respectively. By comparison, as appears from Table 2 shown below, the mean body-weight recorded for the control mice was 18.34 g and 20.6 g respectively. The weight of the minks, GP or pigs was not controlled. However, apparently the pigs developed normally since the slaughterhouse recorded their weight to be similar to that of other animals of the same age. The histological studies carried out on the skin of the mice and minks receiving the highest ginseng dose, did not reveal any changes.

TABLE 2

Example 5. Safety assay: Mice - weight controls. The results show the groups weight mean value in grams.

| Group no. | Ginseng dose/ mouse | Grams on Day 0 | Grams on Day 4 PI* | Grams on Day 7 PI* |
|---|---|---|---|---|
| 1 | 100 μg | 18.78 | 20.76 | 20.34 ± 1.56 |
| 2 | 50 μg | 19.08 | 20.48 | 20.17 ± 1.09 |
| 3 | 20 μg | 18.92 | 21.12 | 21.32 ± 2.40 |
| 4 | 10 μg | 18.14 | 20.86 | 21.02 ± 2.88 |
| 5 | 0 | 18.34 | 20.44 | 20.60 ± 2.26 |

*PI = post ginseng injection

3.6 Results of Example 6

Assay of Haemolysis

At the concentrations assayed, ginseng did not cause haemolysis of bovine RBC's but does have a small effect on swine and chicken RBC's. The highest haemolytic activity was recorded in the assays carried out with the RBC's of GP as shown in Table 3 below. However, it was also noted that the GP RBC's showed the highest degree of spontaneous haemolysis.

TABLE 3

The haemolytic activity of various doses of CH-GS on erythrocytes from different species. The results are presented as the absorbance mean-value obtained from two replicates.

| RBC Species | Amounts of CH-GS in µg/ml | | | |
|---|---|---|---|---|
| | 0 | 1000 | 1500 | 2000 |
| Swine | 0.082 | 0.110 | 0.120 | 0.120 |
| Bovine | 0.094 | 0.052 | 0.050 | 0.054 |
| Chicken | 0.090 | 0.181 | 0.220 | 0.310 |
| Guinea Pig | 0.218 | 0.805 | 0.840 | 1.130 |

3.7 Results of Example 7
Absorption Assays

The quantity of free ginseng detected in the supernatant obtained from the sample incubated with Al(OH)3 gel was found to be greatly reduced from 2 mg to 0.375 mg/ml. By comparison the sample incubated with NaCl-sol. Showed 1.23 mg ginseng/ml. The haemagglutination assay carried out for detecting free PPV antigen in the supernatant of the $Al(OH)_3$-ginseng adjuvanted vaccine, demonstrated that the antigen was completely adsorbed by the gel.

Part II

Below, it will be described how aluminium hydroxide-adjuvanted vaccines against porcine parvovirus and *Erysipelothrix rhusiopathiae* infections were tested in pigs, with and without the addition of ginseng. As in Part I, the tests were carried out in laboratory animals using a viral antigen, it was interesting to investigate if ginseng also has an adjuvant effect with bacterial antigens and if it can be used as a co-adjuvant in swine vaccines. Therefore, two different batches of licensed vaccines against *Erysipelothrix rhusiopathiae* and porcine parvovirus infections were selected and tested on pigs. The two vaccines used in the present experiments were licensed ones and contained inactivated antigens. The antibody response to procine parvovirus was assayed by haemagglutination inhibition tests whereas the immune response to *Erysipelothrix rhusiopathiae* was evaluated by the mouse potency test and ELISA. Antibodies to the 64–66 kD-glycoprotein, the protective antigen of the *Erysipelothrix rhusiopathiae*, were determined by immunoblotting.

4. MATERIAL AND METHODS 4.1 Ginseng

The ginseng used in this study was a dry extract prepared from the Panax ginseng C. A. Meyer-root and was provided free of charge by the Pharmaceutical Co. Ltd. (Chiatai Qingchubao, People's Republic of China). Before use, the ginseng was re-suspended in a physiological NaCl solution (saline) and added to the vaccines at a final concentration of 2 mg ginseng per 2 ml dose of vaccine.

4.2 Antigens

The vaccines included two antigens; binary ethylenimin-inactivated porcine parvovirus (PPV) and formalin-inactivated *Erysipelothrix rhusiopathiae* (*E. rhusiopathiae*) serotype 2. The strain R9 of *E. rhusiopathiae* serotype 1, isolated in Sweden, was used as challenge material in the erysipelas-mouse potency test and for preparing the bacterial antigens used in the ELISA and immunoblot analyses.

4.3 Vaccines

Samples from two commercially available lots of vaccines, which in this study were named vaccine-1 (vacc.1) and vaccine-2 (vacc.2), were tested with and without the addition of ginseng. Each vaccine contained 2,560 haemagglutination units (HAU) of inactivated procine parvovirus and inactivated *E. rhusiopathiae* serotype 2 bacteria, corresponding to 50 protective international units (I.U.) per dose. Both vacc.1 and vacc.2 contained 50%, v/v aluminium hydroxide. Samples of the vaccines described above were mixed together with a ginseng-solution to a final concentration of 2 mg ginseng per 2 ml dose of vaccine. Next, the mixtures were incubated at 4° C. under continuous stirring for seventy-two hours before use. The vaccines were named vacc.1-GINSENG and vacc.2-GINSENG respectively. Apart of the vaccines listed above, the study also included the test of a standard Erysipelas vaccine containing 58 LU.

4.4 Vaccination of Pigs

The animals included in the evaluation of the vaccines were five-month-old, specific pathogen-free pigs (No.14). They were moved to our experimental facilities, two weeks before vaccination and were kept isolated during the experiment. The pigs were divided into four vaccination groups of three animals each, and one control group of two animals. The pigs were injected intramuscularly with 2 ml of one of the vaccines listed above; the injections were given twice with a three week interval between them. Blood samples were taken before vaccinations and 2, 3 and 4 weeks after the second injection. The animals included in group 1 were immunized with vacc.1, the ones in group 2 with vacc.1-GINSENG, the pigs in group 3 with vacc.2 and the ones in group 4 with vacc.2-GINSENG.

5. EXAMPLES 5.1 Example 1
Erysipelas Mouse Potency Test (Immune Response)

The mouse potency test was carried out according to the guidelines given by the European Pharmacopoeia for batch evaluation of the licensed erysipelas vaccines for swine, as follows: 270 female NMRI-mice from our own breeding house were randomly selected and moved to the test facilities four days before vaccination. The mean body weight of the mice was approximately 20 grams.

The animals were divided into 15 vaccination groups with 16 mice in each group and into 3 control groups with 10 mice each. One vaccination group was used for each vaccine dilution. Before vaccination, the standard vaccine was diluted with saline to a concentration of 8, 4, 2, 1 or 0.5 I.U./ml. The two licensed test vaccines were also diluted with saline to give 1:10, 1:20, 1:40, 1:80 and 1:120 vaccine solutions. The mice were injected subcutaneously with 0.5 ml diluted vaccine using 16 mice for each vaccine solution. The mice included in the three control groups were injected in the same manner with 0.5 ml saline. Twenty-one days after vaccination, all immunized mice including those from control group number 1, were inoculated intraperitoneally with 0.5 ml of *E. rhusiopathiae* (strain R9, serotype 1) bacteria suspension (challenge suspension ) containing 1 LD/100. The challenge suspension was further diluted 10 and 100 folds. Thereafter, the suspensions were used for injecting the mice in control groups 2 and 3, respectively. All inoculated animals were observed daily for 8 days, and the number of survivors recorded.
Serological Tests 5.2 Example 2

Haemagglutination Inhibition Assay (Antibody Response)

The antibody response to PPV-virus of the vaccinated pigs was assayed by haemagglutination inhibition (HI) tests. The HI-test was carried out in V-bottomed microplates using a 0.5% suspension of guinea-pig red-blood cells and 16 HAU/50 µl of PPV-virus (Rivera E, Sjöland L, Karlsson K. A. A solid phase fluorescent immunoassay for the rapid detection of virus or antibodies in fetuses infected with porcine parvovirus. *Arch Virol* 1986; 88:19–26).

5.3 Example 3

ELISA (Immune Response)

The *E rhusiopathiae* (strain R9, serotype 1) antigen used for sensibilising ELISA-Nunc MaxiSorp microplates was prepared as previously described for a Pseudomonas-EILSA (Rivera E, Jackert-Jernberger M, Mejerland T, Karlsson K. A. Evaluation of protein A and protein G as indicator system in a ELISA for detecting antibodies in mink to *Pseudomonas aeruginosa*. *Vet Microb* 1994;42:265–271). In short, 100 µl/well of bacterial antigen containing 2 µg protein per ml coating buffer was incubated at 37° C. for 48 hours. Thereafter, the plates were washed carefully and the free-binding sites in the wells were blocked using a blocking buffer containing casein and tween-20 (Rivera et al., 1994, supra). Test samples, 100 µl diluted 1:100, were pipetted into each of two wells. The plates were incubated at 37° C. for 30 min. Thereafter, the plates were carefully washed. Antigen-antibody complexes were detected by means of a peroxidase-conjugated protein-G (Bio Rad Laboratories, Richmond, Calif., USA) diluted 1:10,000. The plates containing the conjugated protein-G (100 µl/well) were incubated and washed again as described above. Then, the plates were incubated at room temperature for 15 min. with the TMB-substrate (200 µl/well). The reaction was stopped with 50 µl/well of 2 M $H_2SO_4$. Next, the optical density of the reactions was measured at 450 nm. using a spectrophotometer.

5.4 Example 4

Immunoblotting

The *E. rhusiopathiae* (strain R9, serotype 1) used for preparing bacterial antigens for immunoblot analyses was first cultured on blood agar plates and then overnight at 37° C. using a modified Feist medium, a serum-free medium shown to enhance the bacteria production of the 64–66 kD glycoprotein, the antigen involved in immunity to swine-erysipelas (Groschup M H, Timony J F. Modified Feist broth as a serum-free alternative for enhanced production of protective antigen of *Erysipelothrix rhusiopathiae*. *J Clin Microbiol.* 1990; 28(11):2573–2575). After incubation, the bacteria were harvested by centrifuging and thereafter, the cells were washed twice by centrifuging and using distilled water. After that, the bacterial-protein was extracted with EDTA as previously described (Groschup M H, Cussler K, Weiss R, Timoney J F. Characterisation of a protective antigen of *Erysipelothrix rhusiopathiae*. *Epidemiol Infect* 1991;107:637–649). Next, the protein extract was concentrated using a centrifugal-concentrator Filtron 50K (Makrosep™, Pall Gelman Sciences, Lund, Sweden) diluted and heated 10 min. at 70° C. in NuPAGE™ LDS Sample buffer with NuPAGE™ Reducing Agent (Novex, San Diego, Calif.). 10 µl was loaded onto a 1 mm 4–12% NuPAGE™ Bis-Tris gel, separated together with Seeblue™ Pre-Stained standard in NuPAGE™ MOPS SDS Running Buffer under reducing conditions (Novex, San Diego, Calif.) and blotted onto nitro-cellulose (BA 85, Schleicher and Schuell, Dassel, Germany). Thereafter, the membranes were first incubated in a 5% dry milk solution followed by a 2 h incubation with sera from vaccinated pigs diluted 1:100 in phosphate buffered saline containing 1% dry milk and 0.1% Tween 20 (serum diluent). Next, the preparations were washed three times and incubated for 2 h with HRPO-conjugated rabbit anti-swine immunoglobulins (Dako A/B, Glostrup, Denmark) diluted 1:3000 in serum diluent. After a new wash cycle, the reaction was developed using FAST-DAB with metal enhancer (Sigma, USA).

5.5 Example 5

Safety

The vaccinated pigs were observed daily for a period of eleven weeks. Reactions at the injection site or changes in the animals behaviour were recorded.

6. RESULTS

As discussed in more detail below the examples above shows that the addition of ginseng potentiated the vaccines' effects without altering their safety. Both the antibody titres against the viral as well as the bacterial antigens were higher in the sera from the pigs immunised with the vaccines containing ginseng than were the titres recorded for the animals injected with the corresponding vaccine without ginseng. Thus, aluminium hydroxide and ginseng acted synergistically.

The vaccines used in the evaluations varied in their immunogenic potency. However, after the addition of 2 mg ginseng per vaccine dose, the less immunogenic vaccine proved to be as potent as the better vaccine without ginseng. Thus demonstrating that the use of ginseng as a co-adjuvant provides a simple, safe and cheap alternative for improving the immunogenic potency of aluminium hydroxide adjuvanted vaccines or vaccines in general.

6.1 Results of Example 1

Mouse Potency Test (Immune Response)

The results presented in Table 4 below demonstrate that vacc.1 was more immunogenic than vacc.2. and induced a better protection. Eight days after infections, the number of survivors recorded for each of the groups immunized with vacc.1 was higher than the number of survivors recorded for the groups of mice injected with the corresponding dilution of the vacc.2. Furthermore, it was found that vacc.1 was even more potent than the standard vaccine, as shown in Table 4. The number of survivors in controls groups 1, 2 and 3 was 0, 1 and 6, respectively (data not shown).

TABLE 4

Example 1: The mouse potency test. Percent of survivors, eight days after infection with live *Erysipelothrix rhusiopathiae* serotype 1.

| Vaccine Dilution's | | Percent of Survivors | | |
|---|---|---|---|---|
| test vacc | standard | vacc. 1 | vacc. 2 | standard |
| 1:10 | 8 I.U. | 93.75 | 68.75 | 87.50 |
| 1:20 | 4 I.U. | 87.50 | 43.75 | 31.25 |
| 1:40 | 2 I.U. | 93.75 | 6.25 | 25.00 |
| 1:80 | 1 I.U. | 37.50 | 18.75 | 0.00 |
| 1:120 | 0.5 I.U. | 31.20 | 6.25 | 0.00 |

Serological Tests

6.2 Results of Example 2

Haemagglutination Inhibition Assay (Antibody Response)

As seen in Table 5 below, vacc.1 induced higher HI-titres of anti-PPV antibodies than did vacc.2. However, after the addition of ginseng, both vaccines become more potent inducing higher antibody titres than the same vaccine injected without ginseng. Furthermore, the least immunogenic vaccine (vacc.2) proved, after the addition of ginseng, to be even more potent than vacc.1 used without ginseng. In all cases, the highest antibody titres were recorded by week 3 after the second immunization, as shown in Table 5. At the end of the evaluation, the vaccines containing ginseng induced 2.66 and 2.33 fold more antibodies than did the ginseng-free vaccines.

TABLE 5

Determination of the antibody response to PPV-virus as assayed by HI-tests. The results are presented as the group-titre mean value.

| Vaccine | The group mean antibody titres ± SD at week | | | |
|---|---|---|---|---|
| | 0 | 2 PB* | 3 PB* | 4 PB* |
| vacc. 1 | 10.0 ± 0.0 | 80.0 ± 0.0 | 106.0 ± 37.1 | 80.0 ± 0.0 |
| vacc. 1-GINSENG | 13.3 ± 4.7 | 320.0 ± 0.0 | 320.0 ± 0.0 | 213.3 ± 75.4 |
| vacc. 2 | 13.3 ± 4.7 | 66.6 ± 18.9 | 106.0 ± 37.7 | 40.0 ± 0.0 |
| vacc. 2-GINSENG | 13.3 ± 4.7 | 173.3 ± 14.6 | 186.0 ± 49.7 | 93.0 ± 30.8 |

PB* = post booster

6.3 Results of Example 3

ELISA

Concerning antibodies to *E. rhusiopathiae*, the ELISA demonstrated that even in this case vacc.1 was more potent than vacc.2 (FIG. 3). The ELISA results are in accordance with those obtained from the mouse potency test (Table 3) where vacc.1 protected a larger number of mice than did vacc.2. Furthermore, similar to the antibody response to PPV, the serum from the pigs immunized with vacc.1-GINSENG or vacc.2-GINSENG recorded higher antibodies titres than the serum from the pigs injected with the ginseng-free vaccines (FIG. 3). Moreover, after the addition of 2 mg ginseng per vaccine dose, the less immunogenic vaccine (vacc.2) proved to be as potent as the better one (vacc.1) when it was injected without ginseng. FIG. 3 also illustrates that the antibody titres induced by the vaccines containing only $Al(OH)_3$ (vacc.1 and 2) decrease with time, while the titres recorded for the vaccines containing $Al(OH)_3$ and ginseng remain almost constant. The results from the HI-test and ELISA demonstrated that ginseng and $Al(OH)_3$ acted synergistically, thereby improving the antibody response to both PPV and *E. rhusiopathiae*.

6.4 Results of Example 4

Immunoblotting

The immunoblot assay (FIG. 4) revealed that the sera obtained from the animals immunized with the vaccines containing ginseng, react more strongly with the proteins in the 64–66 kD area shown to contain protective glykoproteins of *E. rhusiopathiae* (Groschup et al., 1991, supra), than do the sera from animals injected with the same vaccine without the addition of ginseng. In general, sera from the "ginseng-pigs" bind strongly with all *E. rhusiopathiae* proteins. The data obtained from the ELISA, immunoblot analyses and the mouse potency test further confirm the serological cross-reaction between *E. rhusiopathiae* serotype 1 and 2, since the vaccines included erysipelas antigen serotype 2 and the evaluation of the vaccines was carried out using serotype 1.

6.5 Results of Example 5

Safety

The addition of ginseng to the vaccines did not alter the safety of the vaccines. No reactions at the injection site or changes in the animal behaviour were recorded.

Part III

7. The Adjuvant Effect of the Purified Ginsenosides Rb1 and Rg1 Compared with the one of Total Ginseng In this experiment, the adjuvant effect on porcine parvovirus vaccines of the purified Ginsenosides Rb1 and Rg1 were compared with the effect of total ginseng extract. All vaccines were tested using guinea pigs and contained the same amounts of porcine parvovirus antigen but different adjuvants as listed in table 6. The total amounts of Rb1 and Rg1 were calculated to be the same in the vaccines containing ginsenosides, except in vaccine f, which was tested without adjuvant. The final volume for each vaccine dose was 2 ml and was injected subcutaneously.

The antibody titres in the serum samples were measured by means of a haemagglutination inhibition test. The data are presented (table 6) as the group (nr.5) titre mean value recorded at the time for re-vaccination (booster) and two weeks post booster.

TABLE 6

| Vaccine adjuvant | Antibody titres at | |
|---|---|---|
| | Booster | 2 weeks post booster |
| a) Rb1 | 3 ± 4.0 | 352 ± 235 |
| b) Rg1 | 8 ± 7.4 | 304 ± 192 |
| c) Rb1 + Rg1 | 6 ± 8.0 | 256 ± 78 |
| d) Ginseng extract | 10 ± 8.9 | 832 ± 384 |
| e) Ginseng extract + $Al(OH)_3$ | ca. 10 ± 3 | 6826 ± 2413 |
| f) NaCl | 7 ± 7.4 | 292 ± 66 |

The results presented in table 6 demonstrate that purified ginsenosides tested alone (vaccine a and b) or together (vaccine c) induced almost the same antibody titres as the vaccine tested without adjuvant (vaccine f). On the contrary, the vaccine containing total ginseng extract (vaccine d), clearly potentiate the antibody response to PPV-virus, indicating that the content of the total ginseng extract is necessary for stimulating an enhanced antibody response. The adjuvant effect of ginseng is likely the consequence of a summary of effects induced by all ginsenosides present in the extract. However, in all experiments the best adjuvant effect was obtained when both $Al(OH)_3$ and ginseng extract were included in the vaccines (vaccine e).

8. Analysis of Ginseng Extract from Panax Ginseng Root

The ginsenoside content of the extract used in the other experiments (sample 1) was determined (table 7) by HPLC according to Journal of Chromatography, 1990, 504:139–149. Further, another extract, produced according to the same procedures as for sample 1, was analysed according to the same HPLC-method.

TABLE 7

| Ginsenoside | Content % | |
|---|---|---|
| | Sample 1 | Sample 2 |
| Rg1 | 1.32 | 0.08 |
| Re | 2.21 | <0.05 |
| Rb1 | 13.96 | 4.15 |
| Rc | 6.62 | 0.55 |

TABLE 7-continued

| | Content % | |
|---|---|---|
| Ginsenoside | Sample 1 | Sample 2 |
| Rb2 | 6.93 | 0.62 |
| Rd | 5.41 | 1.23 |

This experiment shows that the extract contains several different ginsenosides, which add up to 36.44% (sample 1) of the total content of the extract used in the experiments of this application. Sample 2 shows another extract, showing full adjuvant properties (not shown), but having a lower concentration of ginsenosides.

9. Discussion

According to the present invention, as shown in Part II of the experimental section, it has been shown that ginseng improves the antibody response to the PPV antigen regardless of the administration procedure used (Exp.no.1, 2 and 3). However, the best results were always obtained when Al(OH)$_3$ was also included in the vaccination schedule, which suggests that Al(OH)$_3$ and ginseng act synergistically. Even though the mechanisms behind the Al(OH)$_3$-ginseng interaction are not known, two alternatives may be envisaged, or a combination of both:

1) that the addition of ginseng to the Al(OH)$_3$-adjuvanted PPV vaccines leads to the formation of a larger molecule than the one formed by Al(OH)$_3$-PPV alone; such a reaction would stimulate the antigen-presenting cells in a more favourable manner. This interpretation is suggested, because the results from the absorption assays demonstrated that ginseng is absorbed to the Al(OH)$_3$-gel without interfering with the absorption of the PPV antigen.

2) that Al(OH)$_3$ and ginseng together stimulate a broader spectrum of cells from the immune system than each adjuvant does alone. This is suggested because it has been proven that ginseng promotes the phagocytic activity of macrophages and polymorphonuclear leucocytes (Scaglione et al., 1994, supra; and Hu et al., 1995, supra).

Further, in Part II of the section "Experimental" of the present application, it is demonstrated that the immunogenic potency of aluminium-hydroxide adjuvanted vaccines against PPV and *Erysipelothrix rhusiopathiae* infections can be improved by using ginseng as a vaccine co-adjuvant. Each control of the antibody response to PPV or to *E. rhusiopathiae* demonstrated that ginseng has an enhancing effect on the response to both antigens. Although the *E. rhusiopathiae*-ELISA used for evaluating the adjuvant effect of ginseng is a quantitative rather than qualitative assay, it appears from the immunoblotting analysis of the antibodies that ginseng also potentiates the antibody response to the *E. rhusiopathiae*-protective antigen. Thus, the results according to the present invention may be extended to suggest that the immunogenicity of other vaccines adjuvanted with aluminium hydroxide can also be improved by using ginseng as a vaccine co-adjuvant.

Since the present ginsenosides are saponins, which induce cell-mediated immunity, ginseng offers a good adjuvant alternative for viral vaccines, which, as in the case of live attenuated vaccines, can also vary in potency (e.g. distemper) from lot to lot. This difference in potency results most likely from part of the virus becoming inactivated during lyophilization. Freeze-dried vaccines containing inactivated or a mixture of live and inactivated virus antigen may still be immunogenic if the vaccines are resuspended in a solvent containing ginseng. Such an hypothesis is suggested because the adjuvant effect of ginseng is not dependent on a previous binding reaction with the antigen as demonstrated in our first report about ginseng (part I).

Thus, the results from Part II show: (a) That the synergistic effect of ginseng and aluminium hydroxide on the antibody response to PPV demonstrated in laboratory animals is even true for swine. (b) That in the pig, ginseng also enhanced the antibody response to bacterial antigens e.g. *E. Rhusiopathiae*. (c) That ginseng provides a novel alternative for improving the immunogenic potency of aluminium hydroxide adjuvanted vaccines or vaccines in general, which is simple, safe and cheap.

I claim:

1. A composition capable of enhancing the immunogenic effect of a vaccine, said composition comprising an extract of a ginseng plant and an aluminium salt, and is obtained by a method comprising the steps of:
   (a) providing an extract of a ginseng plant, which extract comprises at least one ginsenoside chosen from Rg1, Re, Rc, Rb1, Rb2 and Rd;
   (b) adding an aluminium salt to the extract.

2. A composition according to claim 1, wherein the ginseng plant is a Panax ginseng root plant.

3. A composition according to claim 1, wherein at least one of the ginsenosides is a tri-terpenoid glycoside.

4. A composition according to claim 3, wherein the tri-terpenoid glycoside comprises the structure of $Rb_1$.

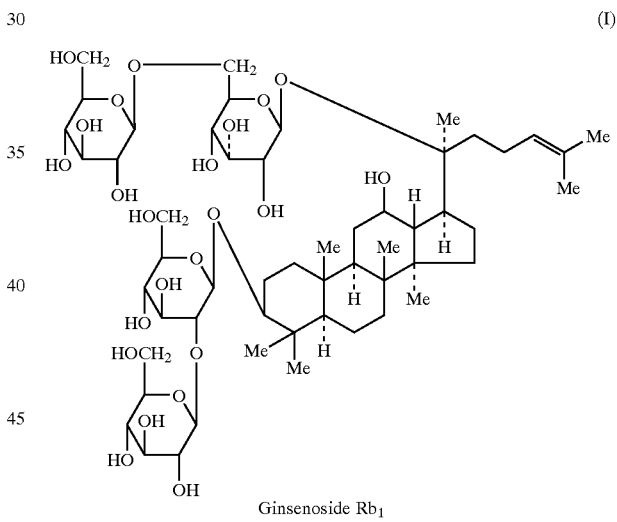

Ginsenoside $Rb_1$

5. A composition according to claim 3, wherein said extract compriseS a plurality of said ginsenosides.

6. A composition according to claim 1, comprising about 5–500 μg, of the at least one ginsenoside.

7. A composition according to claim 1, wherein the extract comprises all of the ginsenosides Rg1, Re, Rb1, Rc, Rb1, Rb2 and Rd.

8. A composition according to claim 1, wherein the aluminium salt is Al(OH)$_3$.

9. A method of manufacturing a pharmaceutical preparation for enhancing the immunogenic effect of a vaccine comprising the step of adding the composition of claim 1 to the preparation.

10. A pharmaceutical preparation comprising the composition of claim 1.

11. A pharmaceutical preparation according to claim 10, which further comprises an immunogenic substance.

12. A kit comprising ingredients capable of enhancing the immunogenic effect of a vaccine, which kit comprises the composition according to claim 1.

13. A kit according to claim 12, wherein the kit further comprises a pharmaceutically acceptable carrier.

14. A kit according to claim 12, which comprises two or more single unit dosages of said composition, one being for an initial administration in connection with a first vaccine dose and the further for administration in connection with a subsequent booster dosage.

15. A kit according to claim 12, which further comprises a vaccine composition.

16. A kit according to claim 12, wherein the ingredients are presented in a form suitable for subcutaneous or intramuscular injection.

17. A kit according to claim 12, which further includes written instructions regarding the use thereof.

* * * * *